US010639007B2

United States Patent
Cole et al.

(10) Patent No.: US 10,639,007 B2
(45) Date of Patent: May 5, 2020

(54) AUTOMATIC TRACKING AND REGISTRATION OF ULTRASOUND PROBE USING OPTICAL SHAPE SENSING WITHOUT TIP FIXATION

(71) Applicant: KONINKLIJKE PHILIPS N.V., Eindhoven (NL)

(72) Inventors: Gregory Cole, Ossining, NY (US); Marissa Patricia Dreyer, Ketchum, ID (US); Bharat Ramachandran, Morganville, NJ (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 162 days.

(21) Appl. No.: 15/529,100

(22) PCT Filed: Dec. 1, 2015

(86) PCT No.: PCT/IB2015/059248
§ 371 (c)(1),
(2) Date: May 24, 2017

(87) PCT Pub. No.: WO2016/088037
PCT Pub. Date: Jun. 9, 2016

(65) Prior Publication Data
US 2017/0290563 A1    Oct. 12, 2017

Related U.S. Application Data

(60) Provisional application No. 62/086,248, filed on Dec. 2, 2014.

(51) Int. Cl.
*A61B 8/00*    (2006.01)
*A61B 5/06*    (2006.01)
(Continued)

(52) U.S. Cl.
CPC ............ *A61B 8/4254* (2013.01); *A61B 5/065* (2013.01); *A61B 34/20* (2016.02);
(Continued)

(58) Field of Classification Search
CPC ....... A61B 8/4254; A61B 34/20; A61B 5/065; A61B 5/6848; A61B 5/6852; A61B 8/12;
(Continued)

(56) References Cited

U.S. PATENT DOCUMENTS 6,612,992 B1    9/2003   Hossack et al.
9,285,246 B2    3/2016   Prisco et al.
(Continued)

OTHER PUBLICATIONS

Shi Chaoyang et al., "Simultaneous catheter and environment modeling for Trans-catheter Aortic Valve Implantation", 2014 IEEE/RSJ International Conference on Intelligent Robots and Systems, IEEE, Sep. 14, 2014, pp. 2024-2029.

*Primary Examiner* — John Bedtelyon

(57) ABSTRACT

A registration device includes an attachment piece (106) configured to conform with and attach to an imaging probe (102), in particular an internal or external ultrasound probe such as a TEE probe. A pathway (105) formed in or on the attachment piece is configured to receive an optical shape sensing device (OSS fiber) such that the optical shape sensing device can free float (no tip fixation) to permit longitudinal twisting within the pathway. The pathway includes a distinctive geometry for shaping the OSS device such that the distinctive geometry provides a template pattern (107) within an image collected using the imaging probe module to permit registration between imaging coordinates and OSS coordinates. A registration module (130) is configured to compare a stored shape template (121) with an image (134) including the template pattern to permit the registration (unique transformation).

15 Claims, 7 Drawing Sheets

(51) Int. Cl.
  *A61B 34/20* (2016.01)
  *A61B 8/12* (2006.01)
  *A61B 5/00* (2006.01)
  *A61M 25/01* (2006.01)
  *G01B 11/24* (2006.01)
  *G01L 1/24* (2006.01)

(52) U.S. Cl.
  CPC ......... *A61M 25/0147* (2013.01); *G01B 11/24* (2013.01); *G01L 1/242* (2013.01); *A61B 5/6848* (2013.01); *A61B 5/6852* (2013.01); *A61B 8/12* (2013.01); *A61B 2034/2061* (2016.02)

(58) Field of Classification Search
  CPC . A61B 2034/2061; G01L 1/242; G01B 11/24; A61M 25/0147
  See application file for complete search history.

(56) References Cited

U.S. PATENT DOCUMENTS

| | | |
|---|---|---|
| 2011/0125022 A1 | 5/2011 | Lazebnik |
| 2011/0202069 A1* | 8/2011 | Prisco ............... G01D 5/35316 606/130 |
| 2013/0028554 A1 | 1/2013 | Wong et al. |
| 2013/0310685 A1 | 11/2013 | Chan et al. |
| 2013/0325387 A1 | 12/2013 | Manzke |
| 2014/0100452 A1 | 4/2014 | Jain |
| 2014/0155737 A1 | 6/2014 | Manzke et al. |
| 2014/0275997 A1 | 9/2014 | Chopra et al. |
| 2015/0038862 A1 | 2/2015 | Gijsbers et al. |
| 2016/0008089 A1 | 1/2016 | Noonan et al. |
| 2016/0015363 A1 | 1/2016 | Tahmasebi Maraghoosh et al. |
| 2016/0213432 A1 | 7/2016 | Flexman et al. |
| 2016/0228199 A1 | 8/2016 | Flexman et al. |
| 2017/0281282 A1 | 10/2017 | Noonan et al. |

* cited by examiner

AUTOMATIC TRACKING AND REGISTRATION OF ULTRASOUND PROBE USING OPTICAL SHAPE SENSING WITHOUT TIP FIXATION

CROSS-REFERENCE TO PRIOR APPLICATIONS

This application is the U.S. National Phase application under 35 U.S.C. § 371 of International Application Serial No. PCT/IB2015/059248, filed on Dec. 1, 2015, which claims the benefit of U.S. Application Ser. No. 62/086,248, filed on Dec. 2, 2014. This application is hereby incorporated by reference herein.

BACKGROUND

Technical Field

This disclosure relates to medical instruments and more particularly to systems, devices and methods with unconstrained shape sensing optical fibers integrated with ultrasound probes.

Description of the Related Art

Optical shape sensing (OSS) uses light along a multicore optical fiber for device localization and navigation during surgical intervention. One principle involved makes use of distributed strain measurement in the optical fiber using characteristic Rayleigh backscatter or controlled grating patterns. The shape along the optical fiber begins at a specific point along the sensor, known as the launch point (or z=0), and the subsequent shape position and orientation are relative to that point. For meaningful clinical use, shape-sensed devices need to be registered to an imaging frame of reference (such as a pre-operative computed tomography (CT) image or a live fluoroscopy image).

In multi-tether shape sensing, where multiple devices are enabled with optical shape sensing, each of these devices needs to be registered to an imaging frame of reference. Alternatively, if one device is registered to the imaging frame of reference then subsequent devices can simply be registered to that first device. Registration between devices is known as 'shape-to-shape' registration.

While registered, preoperative CT provides a wealth of information useful for an interventional procedure; this information is not live and is not updated in response to conditions during the procedure. Live ultrasound imaging augments this preoperative data and gives the clinician valuable insight during an interventional procedure. However, to maximize the value of this live imaging, the information would need to be registered to patient space and tool space.

SUMMARY

In accordance with the present principles, a registration device includes an attachment piece configured to conform with and couple to an imaging probe. A pathway formed in or on the attachment piece is configured to receive an optical shape sensing device such that the optical shape sensing device can free float to permit longitudinal twisting within the pathway. The pathway includes a distinctive geometry for shaping the optical shape sensing device such that the distinctive geometry provides a template pattern within an image collected using the imaging probe to permit registration between imaging coordinates and optical shape sensing coordinates. Another registration system includes an attachment piece configured to conform with and couple to an imaging probe for an imaging system. A pathway formed in or on the attachment piece is configured to receive an optical shape sensing device such that the optical shape sensing device can free float to permit longitudinal twisting within the pathway. The pathway includes a distinctive geometry for shaping the optical shape sensing device such that the distinctive geometry provides a template pattern within an image collected using the imaging probe. A registration module is configured to compare a shape template stored in memory, which corresponds with the template pattern, with an image including the template pattern to permit registration between imaging coordinates and optical shape sensing coordinates.

A method for registration includes connecting an attachment piece to an imaging probe, the attachment piece being configured to conform with and couple to the imaging probe for an imaging system; placing an optical shape sensing device in a pathway formed in or on the attachment piece, the pathway permitting the optical shape sensing device to free float to permit longitudinal twisting within the pathway, the pathway including a distinctive geometry for shaping the optical shape sensing device such that the distinctive geometry provides a template pattern within an image collected using the imaging probe; and registering a shape template stored in memory, which corresponds with the template pattern, with an image including the template pattern to register between imaging coordinates and optical shape sensing coordinates.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
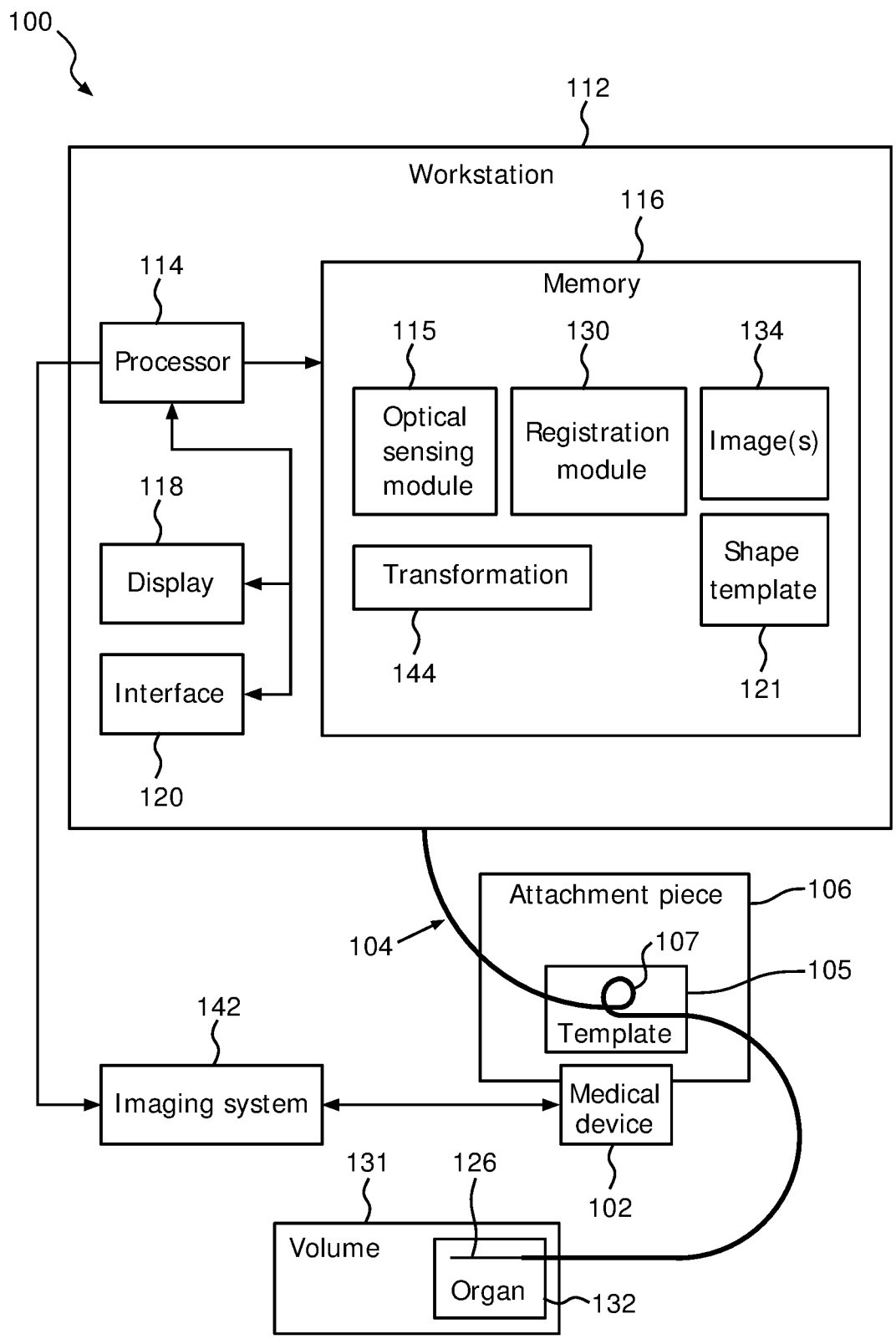
FIG. 1 is a block/flow diagram showing a registration system configured to register an optical shape sensing system with an imaging modality in accordance with one embodiment.

In accordance with the present principles, systems, devices and methods are provided for tracking positions of ultrasound space with respect to optical shape sensing (OSS) space. Ultrasound imaging and, in particular, transesophageal echocardiogram (TEE) imaging, is often used for interventional cardiac procedures and vascular procedures; however, attaching an optical fiber to a TEE probe so as to register OSS space to the TEE image space presents significant mechanical challenges. Present embodiments provide mechanisms which overcome these challenges and are applicable for a variety of ultrasound transducers. In one example, a specific pattern or template is provided as an attachment that clips onto a matrix ultrasound probe. This ensures that the OSS need not be fixed and any portion of the fiber can pass through the probe. By searching along the length of the OSS reconstruction for a matching pattern, the position of the ultrasound probe with respect to the OSS and the ultrasound image/volume with respect to the OSS may be computed. As the ultrasound transducer is moved, the OSS updates the position of the probe and volume in real-time.

To achieve integration of an OSS fiber with a commercial ultrasound probe, an external device type integration may be employed or an internal integration device may be employed. In either case, the fiber may be retrofit or manufactured into the ultrasound probe. An internal integration with the ultrasound probe may come with additional cost and effort to modify a commercial probe's structure. An OSS enhanced ultrasound with a reversible external device is provided to address some of these challenges.

It should be understood that the present principles may be employed for any internal or external probes. In particularly useful embodiments, a transesophageal echocardiogram (TEE) probe, which is used extensively for cardiac procedures or an external matrix array probe (e.g., an X6-1 probe), which is often used for vascular and obstetrics imaging may be employed with OSS, and are employed herein as examples. The present principles address challenges facing OSS integration with probes, especially for a reversible, external integration.

Attaching an OSS fiber to a TEE probe, for example, such that the probes image space can be registered to OSS space faces many challenges. For example, some challenges include fixing the fiber to the probe such that a repeatable six degree of freedom registration to the transducer can be provided; creating a reversible attachment with a small enough profile to be suitable for esophageal insertion; creating a support lumen for the fiber which will accommodate movement of the head and the body of the TEE probe; registering fiber space to ultrasound image space accurately and in real-time; addressing high costs associated with creating permanent changes to the ultrasound probe hardware to fix the tip of OSS fiber, etc.

These limitations can be overcome by finding an alternative to fixing the fiber and creating a reversible low-cost retro-fit attachment. Since a probe head needs to be tracked in 6 DOF, the fiber tip needs to be rigidly fixed to track roll. This is a severe detriment to fiber reliability and performance in a conventional system. By employing a template in accordance with the present principles, the fiber can float without tip fixation. This improves the fiber's reliability, performance, and longevity.

Embodiments in accordance with the present principles may include a hardware integration attaching an OSS fiber to an ultrasound imaging probe and providing methods for registering the OSS fiber to the physical integration. In one embodiment, the physical integration is registered to the probe head. Since some embodiments focus on external methods for integrating an OSS fiber with an ultrasound probe for the purpose of tracking the probe, the fiber can be repeatedly registered to the attachment hardware, which is in turn be registered to ultrasound space. The hardware integration includes the integration of an ultrasound probe with a free-floating OSS fiber.

Ultrasound is an imaging modality which is used in many forms of needle and catheter based interventions to provide real-time image guidance for the interventions. Optical shape sensing can provide insight into these procedures by reconstructing the 3-Dimensional (3D) shape of the lumen in which it is integrated. The combination of the two technologies can permit real-time radiation-free interventions (e.g., no X-rays). The imaging space and OSS information need to be registered to each other. In accordance with the present principles, the OSS fiber can be free-floating (not fixed) and make use of specific shape templates. The ultrasound probe can be moved freely, and the OSS can track the probe using the specific shape template that permits real-time registration.

Unlike shape-to-shape registration, the present principles match a shape feature (like a curvature) to a known template in real-time, which permits for motion-compensated real-time tracking and registration of one or more ultrasound images/volumes and OSS. The present principles also permit the use of OSS with ultrasound using retrofit solutions, without needing any modification of the ultrasound hardware (changes to the probe) or software. This is particularly useful in providing an easy launch of this technology for OSS, e.g., in the cardiac or vascular space. By tracking both the device (i.e., catheter or needle) and the ultrasound transducer, the interventional devices can be registered in the ultrasound image space, even if the origin of the ultrasound image space is non-stationary, and without secondary imaging modalities or tracking methods. This enables advanced functions for the OSS enabled navigation devices and for the interpretation of ultrasound imaging including automatic image slice selection (e.g., tracking the plane of the device, virtual representations of image information such as virtual Intra Cardiac Echocardiogram (ICE), virtual intravenous ultrasound (IVUS) or other methods where small, disposable ultrasound probes are placed on catheters or other devices); image overlay of advanced information (e.g., device position, therapy history and progress, etc.); compounding of ultrasound images (e.g., stitching 3 dimensional ultrasound volumes into larger volumes, overlapping images to improve the resolution of images and reduce motion blur, performing enhanced ultrasound elastography, etc.); registering devices (e.g., using existing registration for the TEE probe in an iXR framework (iXR is a method for automatically registering the probe in x-ray space. This is often used in TEE procedures to overlay ultrasound information in x-ray image space), registration of the probe to x-ray space to bridge the registration of x-rays to OSS space, etc.); anatomically intelligent ultrasound used to register ultrasound to patient space and OSS space; etc.

It should be understood that the present invention will be described in terms of medical instruments; however, the teachings of the present invention are much broader and are applicable to any fiber optic instruments. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Referring now to the drawings in which like numerals represent the same or similar elements and initially to FIG. 1, a system 100 for tracking and registering images with shape sensing enabled devices is illustratively shown in accordance with one embodiment. System 100 may include a workstation or console 112 from which a procedure is supervised and/or managed.

Workstation 112 preferably includes one or more processors 114 and memory 116 for storing programs and applications. Memory 116 may store an optical sensing module 115 configured to interpret optical feedback signals from a shape sensing device or system 104. Optical sensing module 115 is configured to use the optical signal feedback (and any other feedback, e.g., electromagnetic (EM) tracking) to reconstruct deformations, deflections and other changes associated with a medical device or instrument 102 and/or its surrounding region. The medical device 102 may include a catheter, a guidewire, a probe, an endoscope, a robot, an electrode, a filter device, a balloon device, or other medical component, etc. In one particularly useful embodiment, the medical device 102 includes an ultrasonic probe with an attachment piece 106 including a fiber carrying template or pathway 105 with a distinctive geometry, which may fit on or over the probe 102 in or through the pathway or template 105. The attachment piece 106 may include a housing, wall or encasement feature of the medical device 102. The attachment piece 106 may include a removable piece (e.g., split-half, a snap-on attachment, etc.) or include a permanent piece of the medical device 102.

The shape sensing system 104 passes into or is otherwise coupled to the template or pathway 105 of the attachment piece 106 on or in the probe 102 and includes one or more optical fibers 126 which are coupled in the system 104 in a set pattern or patterns. The optical fibers 126 connect to the workstation 112. The shape sensing system 104 may also include or be included in a catheter, a guidewire or other medical component, etc.

Shape sensing system 104 with fiber optics may be based on fiber optic Bragg grating sensors. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, strain causes a shift in the Bragg wavelength.

One advantage of this technique is that various sensor elements can be distributed over the length of a fiber. Incorporating three or more cores with various sensors (gauges) along the length of a fiber that is embedded in a structure permits a three dimensional form of such a structure to be precisely determined, typically with better than 1 mm accuracy. Along the length of the fiber, at various positions, a multitude of FBG sensors can be located (e.g., 3 or more fiber sensing cores). From the strain measurement of each FBG, the curvature of the structure can be inferred at that position. From the multitude of measured positions, the total three-dimensional form is determined.

As an alternative to fiber-optic Bragg gratings, the inherent backscatter in conventional optical fiber can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed.

In one embodiment, the template 105 includes a signature fiber geometry or template pattern 107 therethrough. The template pattern 107 includes one or more curves which receive the shape sensing system 104 therein. The template pattern 107 preferably permits the fiber(s) 126 to float within the pathway 105 (no tip fixation). In this way, longitudinal or axial strain does not build up in the fibers.

An image 134 of the shape sensing system 104 within a space or volume 131 can be displayed on a display device 118. The image 134 may be captured using any imaging modality or system 142, preferably using a probe 102. In particularly useful embodiments, the imaging modality or system 142 includes ultrasound (US). Workstation 112 includes the display 118 for viewing internal images of a subject (patient) or volume 131 and may include the image 134 as an overlay or other rendering registered with the shape sensing system 104. Display 118 may also permit a user to interact with the workstation 112 (and may include a touchscreen interface) and its components and functions, or any other element within the system 100. This is further facilitated by an interface 120 which may include a keyboard, mouse, a joystick, a haptic device, or any other peripheral or control to permit user feedback from and interaction with the workstation 112.

To support one goal of tracking the position of ultrasound space with respect to OSS space, there are several considerations regarding attaching an OSS fiber 126 or system 104 to an ultrasound imaging probe 102. A registration module 130 is configured to register the OSS fiber 126 or system 104 to the physical integration (template 105 and/or attachment piece 106). The registration module 130 also registers the physical integration 106 and/or template 105 to the device 102 (e.g., a probe head). The fiber 126 or system 104 can be repeatedly registered to the attachment hardware or template 105, which is in turn registered to ultrasound space. For OSS space to be effectively registered to ultrasound space, the fiber 126 can either be rigidly mounted to the probe 102, or any changes in the relationship between the fiber and the probe 102 may be tracked and updated. However, it would be advantageous if the physical attachment hardware 106, OSS system 104 or lumen/pathway 105 is repeatably attachable to the probe 102 without having to recalibrate the registration between the fiber 126 and the imaging space (that is, e.g., the physical attachment hardware, fiber, lumen or pathway can be attached, removed and reattached as needed). To this end, the template 105, lumen, etc. attaches to the probe 102 in exactly the same way every time (e.g., keyed or fit connection). In addition, the template 105 needs to be rigid enough so that under regular use, the OSS fiber space registered to the template 105 will not shift with respect to ultrasound image space.

For optimal registration of the OSS fiber 126 or system 104 to the physical attachment hardware 106/template 105, the fiber 126 needs to be tracked relative to the probe 102 in such a way that only a single transformation can be used between OSS space and ultrasound space. This can be achieved either statically or dynamically by ensuring that some identifiable portion of the fiber 126, which incorporates orientation and position information, remains consistent with respect to the ultrasound probe. In other words, the attachment hardware or template 105 provides a shaped fiber pathway such that the portion of the fiber which resides within the pathway can be easily identified. Additionally, the shape properties of this pathway should be such that the shape information of the portion of the fiber residing within the pathway can be used to identify the position and orientation of the pathway, which in turn is rigidly registerable to the ultrasound imaging space.

To use a single point along the fiber 126 for registration of the fiber point position to ultrasound space that point needs to be rigidly fixed to the probe 102 or physical attachment hardware 106 or template 105. The point includes position and roll orientation information with respect to a launch point or position of the OSS system 104. Fixing the point ensures that both position and orientation can be tracked after a one-time manual or automatic set up. However, fixing two points of the fiber (launch and registration point) is not ideal—the fiber cannot relax its axial twist, and the path length the fiber sees needs to remain consistent.

For shape recognition registration, a distinctive shape can be employed to obtain both position and orientation information from the fiber 126. If the fiber 126 takes a predefined and immutable path around the probe 102, the curvature and shape information of that path can be used to identify a unique ultrasound image to fiber transformation. A shape template 121 can be created and stored in memory 116, which matches the path that the fiber 126 takes around the probe 102, and an axis defining an origin position and orientation can be defined relative to this shape template 121. The shape template 121 can be registered, statically or dynamically, to the fiber 126 using shape-to-shape registration. Curvature information from the shape template 121 can be used to find the location of the fiber 126 which is in the predefined shape.

In a one-time registration initialization process, a transformation 144 is found between the ultrasound image and the axis defined by the shape template 121. This can be accomplished using a registration phantom, in which a registered fiber is seen clearly in the ultrasound image. Then, the ultrasound image can be matched with the visualization of the registered fiber either manually or automatically. Alternatively, if the location and orientation of the ultrasound image origin is known in relation to points on the probe 102, the registration initialization transformation can be calculated. A one-time registration of the ultrasound image to the shape template 121 combined with a live registration of the shape template 121 to the fiber 126 results in a live ultrasound image to fiber registration.

Some of the benefits of shape based registration are described as follows. Because template registration is independent of axial twist, within shape reconstruction capabilities, twist along the fiber 126 does not need to be constrained with respect to the probe 102. The shape itself (x, y, z positions) will provide any necessary orientation information. A floating tip configuration is beneficial for the fiber 126 in terms of twist, strain relaxation and fiber longevity.

Template registration to the predefined path the fiber 126 takes around the probe 102 is independent of location along the fiber 126. This means that the fiber 126 in its device can slide in relation to the probe 102, giving the potential for added flexibility for the operator. Shape sensed devices (system 104, such as a catheter) need not be custom made for use with an ultrasound probe 102, as long as they are flexible enough to conform to the shape template pathway within the attachment. Multiple probes may be employed along fiber 126 or system 104. The flexibility of using a shape based registration permits for multiple probes to easily be tracked with one device.

Figure 2A:
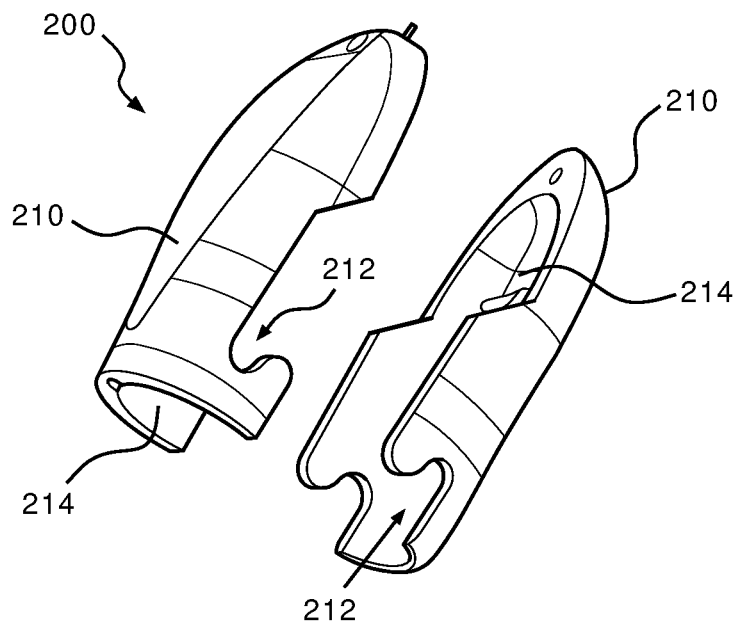
FIG. 2A is a perspective view showing a split-half attachment piece or head cap for a transesophageal echocardiogram (TEE) probe in accordance with one embodiment.
Figure 2B:
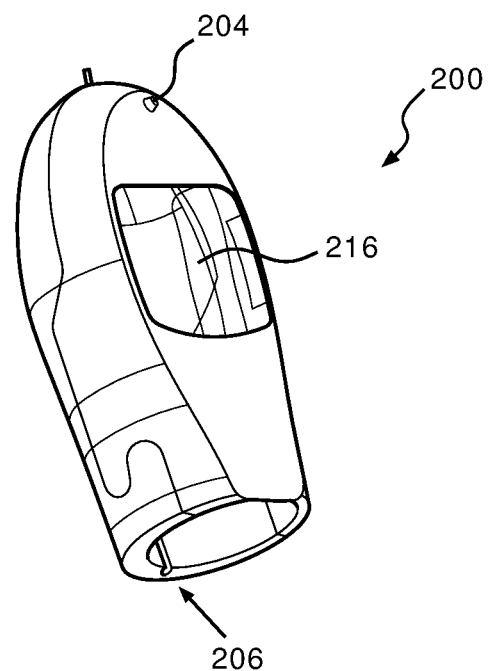
FIG. 2B is a perspective view showing the split-half attachment piece of FIG. 2A closed for use with the TEE probe in accordance with one embodiment.
Figure 2C:
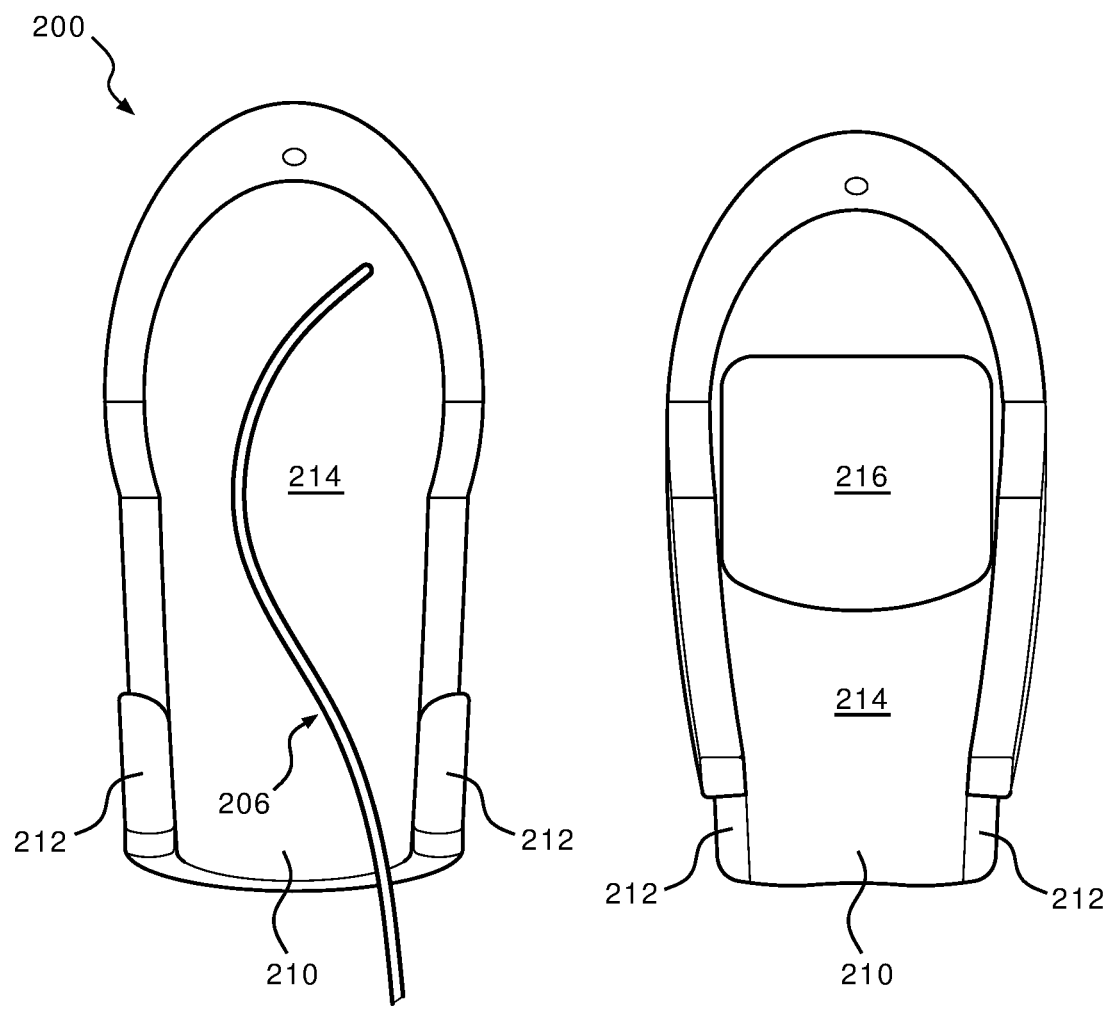
FIG. 2C is an image showing a split-half attachment piece for the TEE probe showing an OSS lumen in accordance with one embodiment.

Referring to FIGS. 2A-2C, a TEE integration cap 200 for a TEE probe is shown in accordance with one illustrative embodiment. The TEE probe is an example of an internal ultrasound probe. By its nature, a head of the TEE probe is designed to fit inside a human esophagus. To maintain this functionality, any attachment needs to have a slim profile that is suitable for insertion into the esophagus as well. In addition, an attachment of a fiber to the head needs to be suitable to create a transformation between fiber space and ultrasound space. To this end, an ultra-low profile head cap 200 is provided. The head cap 200 may be made in a split-half arrangement with halves 210 being manufactured using mold-matched inner surfaces 214 to locate the cap 200 repeatably on the TEE probe (not shown). A contour based clamping mechanism 212 enables a very low profile design, and single attachment screw 204. A lumen or channel 206 is provided within or on the cap 200 for routing an OSS fiber (not shown). A transducer window 216 provides a window for acoustic energy when the cap 200 is in use.

Figure 3:
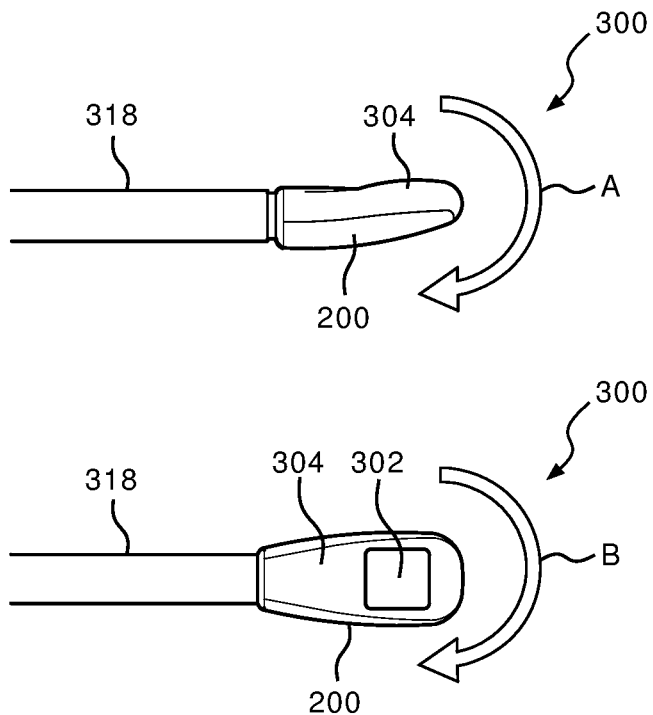
FIG. 3 shows side perspective views of a TEE probe with an attachment piece and showing two degrees of freedom in accordance with one embodiment.

Referring to FIG. 3 with continued reference to FIGS. 2A, 2B and 2C, a TEE probe 300 includes a transducer 302 positioned at the end of a long flexible body or sheath 318, and at a distal tip, the transducer head 200 has two degrees of freedom in bending causing path length changes. FIG. 3 shows the degrees of freedom of a TEE distal portion showing the total path length change in each direction. To track the motion of a TEE probe head 304 and thus track the motion of the ultrasound imaging space, the fiber lumen 206 needs to track head movement of the TEE probe to avoid kinking. Since the lumen 206 will always be offset from the central axis of this bending indicated by arrows A and B, there will be a path length change associated the path of the fiber. To protect the fiber from kinking, this path length change needs to be managed.

This problem is addressed through the use of an elastic fiber lumen 206, 312 (FIG. 4) (e.g., nitinol), which is attached to the probe head 304 (and may be inside or outside of the probe sheath 318) through lumen clips or the like. The fiber lumen 206 (312, FIG. 4) serves several purposes including providing a protected lumen to bring the fiber to or through the head cap 200, resisting bending of the fiber lumen 206, 312 (FIG. 4) to ensure that the fiber always experiences the minimum curvature possible, and providing column strength to push and pull the lumen body in response to path length changes at a distal neck of the probe 300.

Figure 4:
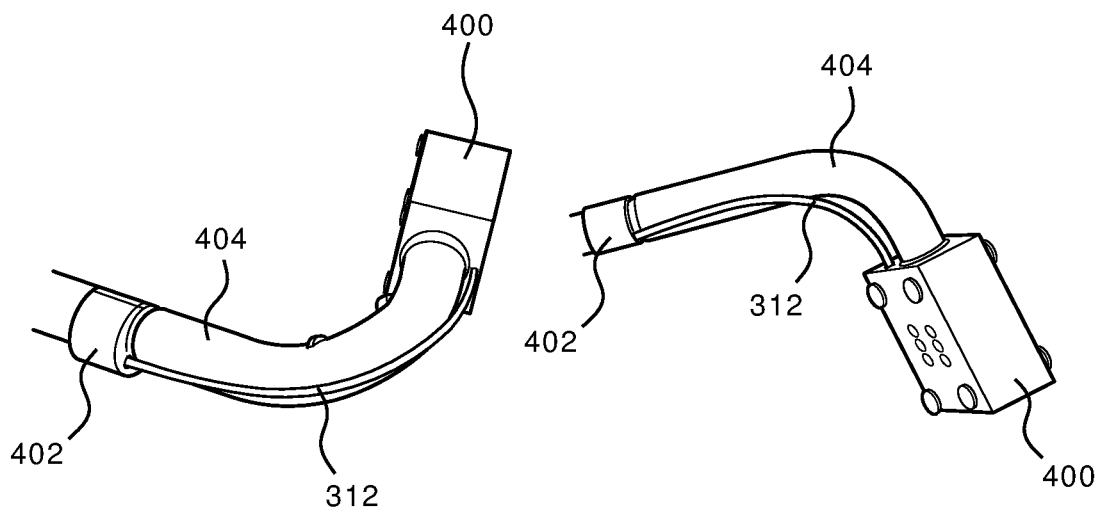
FIG. 4 shows side perspective views of a TEE probe having an attachment piece therein and a protective external lumen for an OSS fiber in accordance with one embodiment.

Referring to FIG. 4, an illustrative embodiment shows a lumen and clip support system developed to address the purposes described with reference to FIG. 3. The degrees of freedom of the distal portion of the TEE probe 300 are shown for a prototype head cap 400. A lumen guide clip 402 is shown supporting an armored fiber lumen 312. The armored fiber lumen 312 receives the OSS fiber and remains protected and offset from a probe 404 while providing a full range of motion for the probe 404.

Figure 5:
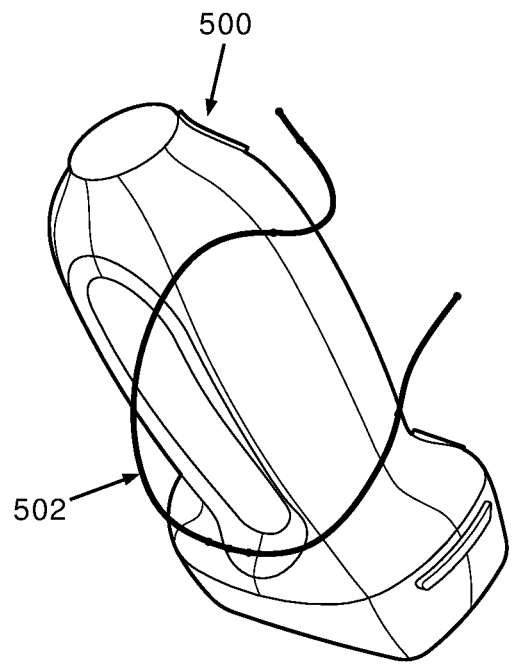
FIG. 5 shows a perspective view of an external imaging probe onto which an attachment piece can be affixed, and an illustrative fiber path relative to the probe in accordance with one embodiment.

Referring to FIG. 5, an external probe 500, such as an X6-1 probe, available commercially from Philips®, is designed to provide an ergonomic shape. Despite this constraint, this type of probe offers significantly more spatial freedom than the TEE probe or other internal probes as this is an external probe and does not need to fit within the body. FIG. 5 shows a fiber 502 along its path without an attachment piece or cap 600 in place. The attachment piece or cap 600 is shown in FIG. 6.

Figure 6:
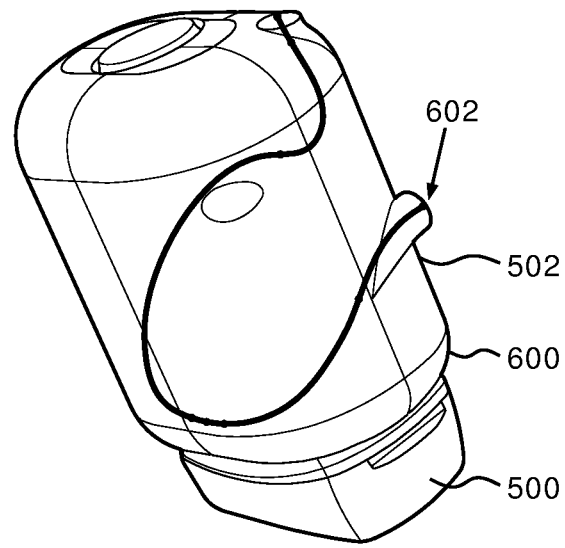
FIG. 6 is a perspective view of an external imaging probe having an attachment piece affixed thereto with an OSS fiber provided in the attachment piece in accordance with one embodiment.

Referring to FIG. 6, a custom-designed probe attachment piece or cap 600 is depicted that provides a unique lumen 602 to guide a fiber 502, protected by a sheath (or other structure), through a path which is fixed with respect to the probe 500. While the fiber is free to translate and rotate, the template shape path does not change with respect to the ultrasound probe or transducer 500, and therefore the ultrasound image space. A cross-section of the lumen 602 can be sized to allow for versatility in fiber sheaths. For example, the attachment piece 600 can be compatible with a catheter, guidewire, or sheath which culminates in a needle, etc. The lumen 602 may be constructed such that the fiber 502 is pushed through the lumen 602, or placed into a split lumen to permit for rigid end pieces (e.g., a needle, etc.).

Figure 7:
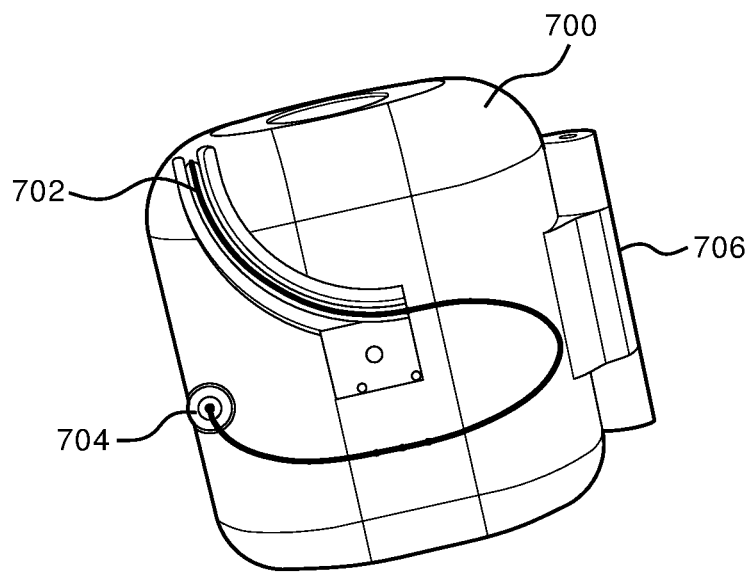
FIG. 7 is a perspective view of a hinged attachment piece affixed to a probe and having an OSS fiber provided in the attachment piece in accordance with another embodiment.

Referring to FIG. 7, in one embodiment, an attachment piece 700 can be constructed with a split lumen 702 and a closed lumen 704. A cover piece (not shown) is clamped onto the split lumen 702 to create a full lumen. Attachment pieces can be designed to include fully split or fully closed lumens or combinations thereof. The attachment piece 700 includes a hinge 706 to hold the portions of the piece 700 together or to open them to access a center portion of the piece 700.

Figure 8:
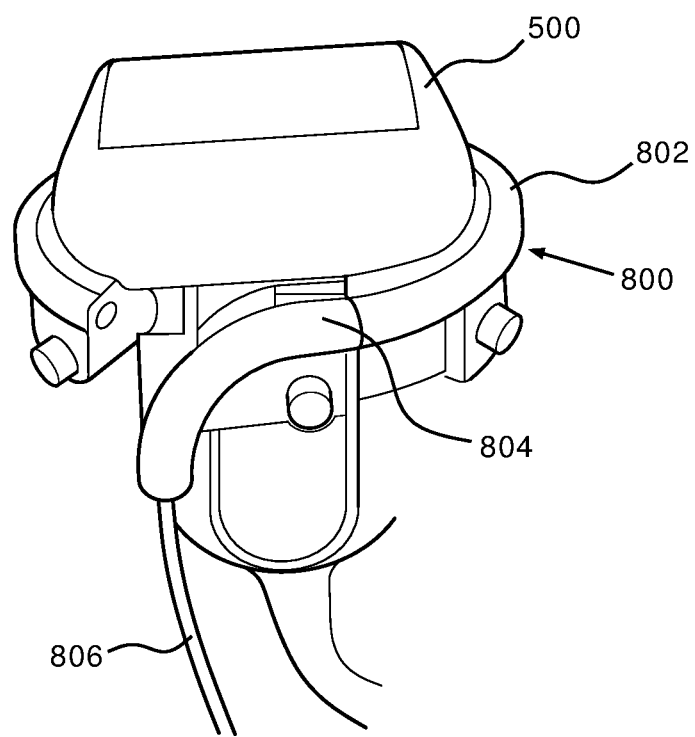
FIG. 8 is a perspective view of an attachment piece retrofitted to a probe and having an OSS fiber provided in the attachment piece in accordance with another embodiment.

Referring to FIG. 8, another embodiment depicts a retrofit attachment piece 800 solution on an external X6-1 probe 500. The piece 800 includes one or more circumferential curved portions 802 and one or more longitudinal curved portions 804 to create a distinctive curve signature for an OSS fiber system 806 disposed therein. The defined features permit for real-time tracking and registration of the probe 500. While the external probe attachments are illustratively depicted for the X6-1 probe, it should be understood that the present principles are applicable to any ultrasound probe.

The present principles can similarly be applied to other external or internal probes. A probe could be manufactured with a lumen in accordance with the present principles or the design of the external attachment could be altered to best appeal to clinicians. For all attachment pieces in accordance with the present principles, the fiber path should be non-symmetrical and not mimic naturally induced curvature patterns, to enable a distinctive shape based fiber to ultrasound volume registration.

Figure 9:
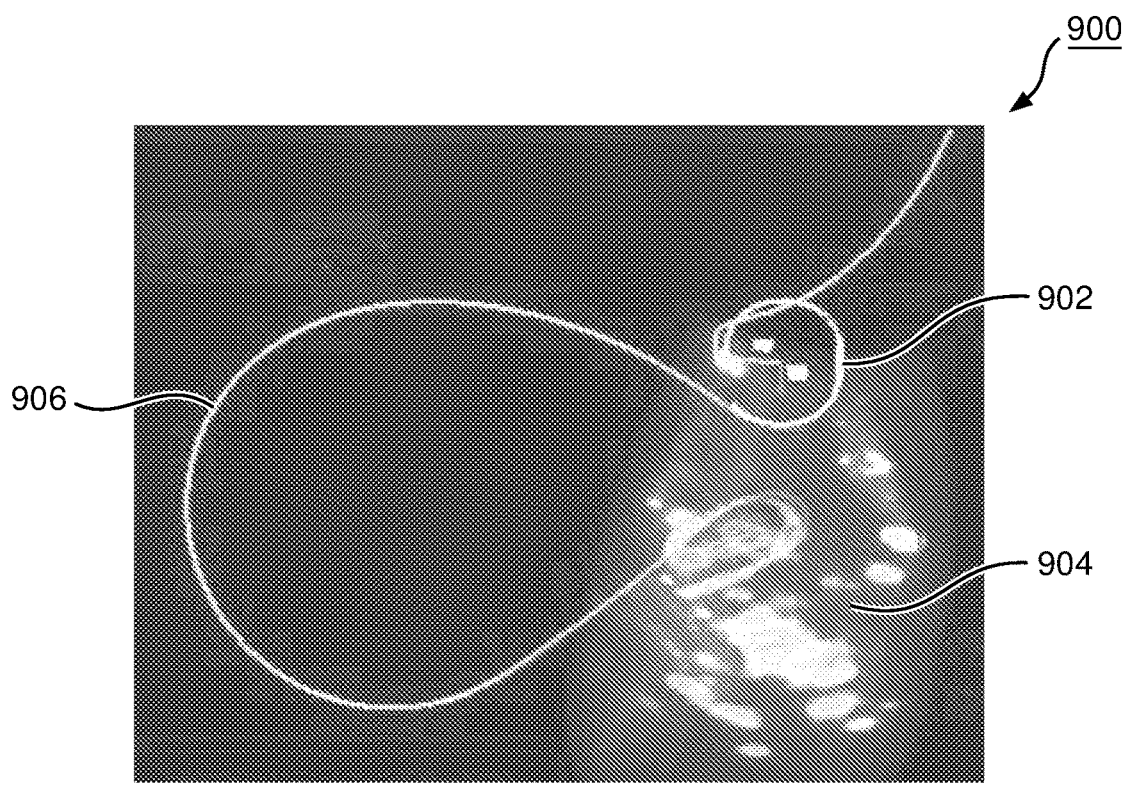
FIG. 9 is an image showing a shape template matched to a template pattern to register an OSS coordinate system to an ultrasound coordinate system in accordance with the present principles.

Referring to FIG. 9, an image 900 is shown depicting an ultrasound phantom 904 having a shape sensing enabled catheter 906 passing therein. The catheter 906 is wrapped about an attachment piece with a template pattern 902. Known geometry of the template pattern 902 appears in the phantom 904 for the OSS fiber of the catheter 906 which continues on from the template pattern 902. Based on the position where the OSS catheter 906 matches the template pattern 902, the volume of the phantom 904 is transformed and placed, ensuring real-time registration.

The present principles have been presented illustratively for TEE and external US probe configurations; however, the present principles apply to any integration of optical shape sensing into medical devices for navigation in the body or in mechanical systems or devices. These principles are particularly relevant to multi-tether applications where two devices are employed that have a known geometry with respect to each other and where shape-to-shape registration is a consideration. Applications include use of guidewires and catheters (manual and robotic), but can be extended to endoscopes, bronchoscopes, and other such applications. The OSS fibers may employ different physical parameters, e.g., Rayleigh scatter (enhanced and regular), Fiber Bragg implementations, other scatter types, etc.

Figure 10:
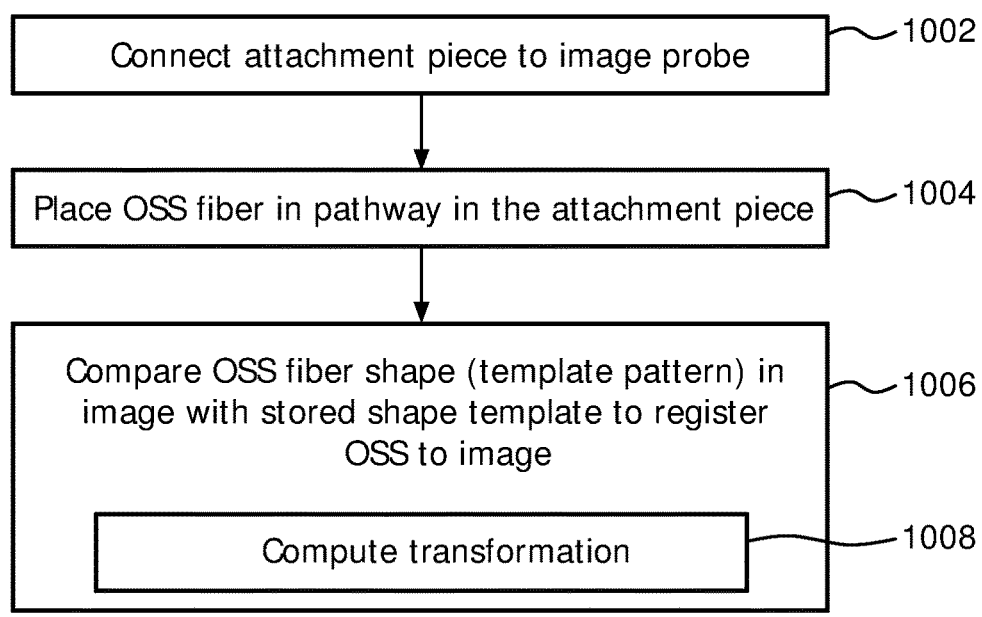
FIG. 10 is a flow diagram showing a method for registration of an optical shape-sensing fiber to an imaging modality in accordance with an illustrative embodiment.

Referring to FIG. 10, a method for registration is illustratively shown in accordance with illustrative embodiments. In block 1002, an attachment piece is connected to an imaging probe. The attachment piece is configured to conform with and attach to the imaging probe for an imaging system. The attachment piece may be split half, slide over a top of the probe, connect to the probe, be integrated into a housing or other feature or include any other configuration in accordance with the present principles. The imaging probe may include a TEE probe, an external ultrasound probe or other probe or device.

In block 1004, an optical shape sensing device is placed in a pathway formed in or on the attachment piece or housing. The pathway permits the optical shape sensing device to free float to permit longitudinal twisting within the pathway. In this way, a tip of the device is not fixed. The pathway includes a distinctive geometry for shaping the optical shape sensing device such that the distinctive geometry provides a template pattern within an image collected using the imaging probe.

The pathway may include a lumen for receiving the optical shape sensing device therein where the optical shape sensing device is threaded through the lumen. The pathway may alternately include a split lumen configured to be opened for receiving the optical shape sensing device having an instrument coupled on a distal end portion thereof. In one embodiment, the pathway extends longitudinally along a cable of the probe, the pathway including a protective lumen coupled to an exterior of the cable. This is particularly useful where the imaging probe includes a TEE probe.

In one embodiment, multiple attachment pieces may be employed with multiple probes and a single OSS fiber. In another embodiment, the OSS fiber is included in a catheter, guidewire or other instrument.

In block 1006, a shape template, which is stored in memory, is registered with an image including the template pattern. The template pattern is provided on the attachment piece and corresponds with the stored shape template. The shape template and the template pattern are matched to register between imaging coordinates and optical shape sensing coordinates.

In block 1008, the registration between imaging coordinates and optical shape sensing coordinates may include computing a transformation between the shape template and the template pattern.

In interpreting the appended claims, it should be understood that:

a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for automatic tracking and registration of ultrasound probe using optical shape sensing without tip fixation (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A registration device, comprising:
   an attachment piece configured to conform with and couple to an imaging probe; and
   a pathway formed in or on the attachment piece and being configured to receive an optical shape sensing device such that the optical shape sensing device can free float to permit longitudinal twisting within the pathway, the pathway including a distinctive geometry for shaping the optical shape sensing device such that the distinctive geometry provides a template pattern within an image collected using the imaging probe to permit registration between imaging coordinates and optical shape sensing coordinates.

2. The device as recited in claim 1, wherein the pathway includes a lumen for receiving the optical shape sensing device therein.

3. The device as recited in claim 1, wherein the pathway includes a split lumen configured to be opened for receiving the optical shape sensing device having an instrument coupled on a distal end portion thereof.

4. The device as recited in claim 1, wherein the attachment piece includes a contoured internal profile for receiving the imaging probe therein.

5. The device as recited in claim 1, wherein the pathway extends longitudinally along a cable of the probe, the pathway including a protective lumen coupled to an exterior of the cable.

6. The device as recited in claim 1, wherein the imaging probe includes an internal ultrasound probe.

7. The device as recited in claim 1, wherein the imaging probe includes an external ultrasound probe.

8. A registration system, comprising:
   an attachment piece configured to conform with and couple to an imaging probe for an imaging system;
   a pathway formed in or on the attachment piece and being configured to receive an optical shape sensing device such that the optical shape sensing device can free float to permit longitudinal twisting within the pathway, the pathway including a distinctive geometry for shaping the optical shape sensing device such that the distinctive geometry provides a template pattern within an image collected using the imaging probe; and
   a registration module configured to compare a shape template stored in memory, which corresponds with the template pattern, with an image including the template pattern to permit registration between imaging coordinates and optical shape sensing coordinates.

9. The system as recited in claim 8, wherein the registration module computes a transformation between the shape template and the template pattern.

10. The system as recited in claim 8, wherein the pathway includes a lumen for receiving the optical shape sensing device therein.

11. The system as recited in claim 8, wherein the pathway) includes a split lumen configured to be opened for receiving the optical shape sensing device having an instrument coupled on a distal end portion thereof.

12. The system as recited in claim 8, wherein the attachment piece includes a contoured internal profile for receiving the imaging probe therein.

13. The system as recited in claim 8, wherein the pathway extends longitudinally along a cable of the probe, the pathway including a protective lumen coupled to an exterior of the cable.

14. The system as recited in claim 8, wherein the imaging probe includes an external ultrasound probe.

15. A method for registration, comprising:
connecting an attachment piece to an imaging probe, the attachment piece being configured to conform with and couple to the imaging probe for an imaging system;
placing an optical shape sensing device in a pathway formed in or on the attachment piece, the pathway permitting the optical shape sensing device to free float to permit longitudinal twisting within the pathway, the pathway including a distinctive geometry for shaping the optical shape sensing device such that the distinctive geometry provides a template pattern within an image collected using the imaging probe; and
registering a shape template stored in memory, which corresponds with the template pattern, with an image including the template pattern to register between imaging coordinates and optical shape sensing coordinates.

* * * * *